United States Patent [19]
Agee et al.

[11] Patent Number: 5,868,686
[45] Date of Patent: Feb. 9, 1999

[54] METHOD FOR DETECTING UNPHYSIOLOGIC TENDON TRANSLATION

[75] Inventors: John M. Agee, 77 Scripps Dr. #100, Sacramento, Calif. 95825; Timothy R. Maher, Sacramento, Calif.

[73] Assignee: John M. Agee, Sacramento, Calif.

[21] Appl. No.: 857,174

[22] Filed: May 15, 1997

Related U.S. Application Data

[63] Continuation of Ser. No. 429,935, Apr. 27, 1995, abandoned.

[51] Int. Cl.⁶ .................................................. A61B 5/12
[52] U.S. Cl. .......................................... 600/595; 600/586
[58] Field of Search .................................... 128/739, 741, 128/744, 774, 782, 773; 600/586, 587, 595

[56] References Cited

U.S. PATENT DOCUMENTS

| | | | |
|---|---|---|---|
| 4,622,013 | 11/1986 | Cerchio | 434/118 |
| 4,807,642 | 2/1989 | Brown | 128/733 |
| 4,991,581 | 2/1991 | Andries | 128/715 |
| 5,010,889 | 4/1991 | Bredesen et al. | 128/715 |
| 5,010,890 | 4/1991 | Pfohl et al. | 128/773 |
| 5,022,405 | 6/1991 | Hok et al. | 128/715 |
| 5,027,825 | 7/1991 | Phelphs, Sr. et al. | 128/715 |
| 5,035,247 | 7/1991 | Heimann | 128/715 |
| 5,129,403 | 7/1992 | Henriquez et al. | 128/773 |
| 5,215,100 | 6/1993 | Spitz et al. | 128/741 |
| 5,230,345 | 7/1993 | Curran et al. | 128/739 |
| 5,275,174 | 1/1994 | Cook | 128/782 |
| 5,301,679 | 4/1994 | Taylor | 128/773 |
| 5,305,238 | 4/1994 | Starr, III et al. | 364/569 |
| 5,381,805 | 1/1995 | Tuckett et al. | 128/739 |
| 5,462,065 | 10/1995 | Cusimano | 128/782 |

OTHER PUBLICATIONS

Nakamichi, K., et al., "Restricted Motion of the Median Nerve in Carpal Tunnel Syndrome", From the Department of Orthopaedic Surgery, Toranomon Hospital, Minato–ku, Tokyo, Japan, Journal of Hand Surgery (British and European vol., 1995) 20B: 4; 460–464.

Nakamichi, K., et al., "Transverse Sliding of the Median Nerve Beneath The Flexor Retinaculum", From the Department of Orthopaedic Surgery, Toranomon Hospital, Tokyo, Japan, Journal of Hand Surgery (British vol., 1992) 17B: 213–216.

Robert E. Markisan, Treatment of Musical Hands: Redsign of the Interface, in Hand Clinics, pp. 525–544, vol. 6, No. 3, Pub. by W.B. Saunders Co., Aug. 1990.

*Primary Examiner*—Max Hindenburg
*Attorney, Agent, or Firm*—Morrison & Foerster LLP

[57] ABSTRACT

Keyboard constructions and methods are described which force or provide feedback for finger action that will enhance stability of the carpal tunnel tendons. Methods are described for reducing incidence of carpal tunnel syndrome in a person who operates a keyboard, involving monitoring actuation of switches, measuring a depression characteristic, comparing the depression characteristic with a predetermined value, and creating a signal corresponding to the number of keystrokes executed with a depression characteristic less than the predetermined value. A method is also described for detecting unphysiologic tendon translation denoting tendon instability in the carpal tunnel of a person who engages in repetitive hand motion.

12 Claims, 11 Drawing Sheets

METHOD FOR DETECTING UNPHYSIOLOGIC TENDON TRANSLATION

This is a continuation of application Ser. No. 08/429,935 filed on Apr. 27, 1995 now abandoned.

FIELD OF THE INVENTION

This invention relates to computer keyboards, and more particularly to keyboards and their structures, and the user interface to the same, including both hardware and software, that are ergonomically designed, ideally to prevent the occurrence of, or more practically, to decrease the incidence of carpal tunnel syndrome.

BACKGROUND OF THE INVENTION

Carpal tunnel syndrome is at present the most widespread occupational health hazard in the industrial world, and it is receiving increasing attention from corporate as well as government agencies responsible for occupational health and safety. Many billions of dollars are consumed by this syndrome each year in lost working time and medical treatment. Carpal tunnel surgery is currently one of the most frequently performed surgeries in the United States. Although some of the physiological factors associated with idiopathic carpal tunnel syndrome are well studied and documented, including the increase in carpal tunnel pressure and the non-inflammatory changes in the synovium, the etiology of idiopathic carpal tunnel syndrome remains obscure, and is the subject of continued speculation and scientific study.

Carpal tunnel syndrome is associated with swelling of the carpal tunnel synovium. When synovium harvested at the time of carpal tunnel surgery is examined by conventional light microscopy techniques, it is remarkably normal in appearance and notable for the absence of inflammatory cells. This and other information suggests that the primary pathology is not intrinsic to the synovium itself, but that the synovium becomes swollen and thickened in response to mechanical stresses.

Normal synovial membrane is thin, elastic and compliant in nature. It is mechanically incapable of maintaining the anatomic relationships between the various digital flexor tendons in the carpal tunnel.

In anatomic areas other than the carpal tunnel, the biomechanical effect of each tendon is defined by a discrete fiberosseous tunnel that dictates the moment arm that the tendon utilizes to effect a rotational force or moment on the joint which the tendon is crossing. In the carpal tunnel, a similar stable relationship between the various tendons during wrist extension flexion can only be maintained if there is a synergistic tensioning of all the tendons to form a "dynamic pulley" capable of stabilizing each and every carpal tunnel tendon.

The profundus tendons embrace the dorsal wall of the carpal tunnel. The profundus tendons of the long, ring, and little fingers are cross-linked and thereby present a common muscle tendon unit that trifurcates at the distal end of the carpal tunnel sending separate tendons to the distal joints of the ulnar three fingers. In concert with the index profundus, these tendons mechanically fill the dorsal wall of the carpal tunnel, and as a functional unit, they present a smooth palmar surface to the overlying sublimus tendons and their associated synovial membranes. This surface is further enhanced as a continuous bearing surface by the third and fourth lumbrical muscles that arise from the adjacent sides of the long and ring, and the ring and little finger profundi.

Additional support to the dorsal wall of the carpal tunnel is provided by the first and second lumbrical muscles that arise from the palmar radial sides of the index and long finger profundus tendons. The origin of these unique muscles migrate from a mid-palmar position, with the fingers extended, to a position just proximal to the level of the distal radius, with full finger flexion.

When a singular finger momentarily acts to press a key on a computer keyboard, if only its associated extrinsic flexor muscles contract, while the remaining carpal tunnel flexor-tendon units remain relaxed, and if the wrist position allows some degree of angulation, those tendons under tension will translate across the carpal tunnel. For example, with the wrist extended, the tension for index finger flexion creates a force that attempts to displace the sublimus tendon dorsally. If the dorsal extent of the carpal tunnel is stabilized by active tension in the profundus tendons with or without active contraction of their lumbrical muscles, then the sublimis tendon will be prevented from translating dorsally. Because each carpal tunnel tendon angulates as it extends to its respective digit from the distal end of the tunnel, there is no "safe" position of the wrist that will eliminate these tendon translating forces or even minimize the translation potential of each of them with a defined wrist position at any instant in time. Without the dynamic and synergistic action of all the carpal tunnel muscle tendon units and the lumbricals, the compliant synovium, being incapable of restraining the movement, will be subjected to an undesirable cyclic load including shear stresses and secondary swelling from the same.

These same principles would be operative with the wrist in flexion, and the more palmar sublimi, adjacent to the transverse carpal ligament, would need to actively contract to block palmar translation of the remaining sublimus and profundus muscle tendon units. This concept of synergistic muscle contraction to achieve carpal tunnel tendon stability applies equally to wrist deviations in the radial-ulnar plane or any combination of such deviations with flexion or extension.

Rapid alpha-numeric data entry via currently-available computer keyboards allows the use of relatively small actuating forces Minimal active stability of the distal joints is required, and can be accomplished with contraction of a single extrinsic muscle tendon unit, such as that of the sublimus. This action is further encouraged with longer fingernails, where the nail keeps the person from flexing the distal interphalangeal joint as they strike the keys with the palmar pulp rather than the distal pulp of the tip of the finger or its protruding nail.

The incidence of carpal tunnel syndrome has continued to increase dramatically since the current style electronic keyboard has come into wide usage. The keyboard of the old manual typewriter did not have a significant incidence of carpal tunnel syndrome associated with its usage. There are three significant differences between the old manual (i.e., mechanical) keyboard and the current electronic keyboards, namely, keystroke length, actuation force, (and its variable degree through the stroke length), and key height differential (front to back row key heights). Table 1 is a sample of these differences.

TABLE 1

| Manufacturer | Type | Median Stroke mm | Height Diff. mm | Median Force Kg |
|---|---|---|---|---|
| Sharp | Electronic | 1.8 | 14.2 | 0.044 |
| Apple | Electronic | 1.9 | 9.7 | 0.070 |
| IBM | Electric | 3.7 | 12.7 | near zero |
| Smith-Corona | Electric | 2.7 | 12.7 | 0.078 |
| Olivetti | Manual | 14.7 | 26.9 | 0.910 |

There has not heretofore been provided a keyboard structure which will teach, encourage or even require the keyboard operator to actively recruit the contraction of all (or most of) the muscle tendon units passing through the carpal tunnel in order to stabilize those tendons whose digits are actuating keys.

SUMMARY OF THE INVENTION

The invention provides keyboard constructions which force or provide feedback for finger action that will enhance stability of the carpal tunnel tendons. The simplest embodiment of the invention can utilize a sufficiently stiff spring action that it could not consistently be actuated by a single extrinsic muscle tendon unit (with or without concomitant synergistic contraction of the interosseous and lumbrical muscles).

A second embodiment of the keyboard construction would employ means to measure or calculate the characteristics of each keystroke, including velocity, acceleration, stroke and force. These parameters can then be compared by a microprocessor with ergonomically correct parameters, which are then used to provide an appropriate feedback to the operator. This embodiment, with a change in computer software, can also be ideal for other keyboard studies where velocities, accelerations, and forces are important parameters to measure.

A third embodiment of keyboard construction would position the keys at much different levels reminiscent of mechanical typewriter keyboards. This design requires a more dynamic interface between the fingers and the keys, and it encourages hand use patterns that ensure an active involvement of multiple muscle tendon units that cross the wrist, both across the surface of the carpus or through its tunnel.

The keyboard constructions of the present invention encourage or require the operator to strike the keys with sufficient force and in an appropriate manner such that an active involvement of multiple muscle tendon units that cross the wrist occurs. In other words, unphysiologic tendon translation in the carpal tunnel is minimized or eliminated. This tends to reduce, eliminate or minimize the incidence of carpal tunnel syndrome.

Other advantages of the keyboard constructions of the invention will be apparent from the following detailed description and the accompanying drawings.

Another form of the invention is a method for detecting events related to unphysiologic tendon translation denoting tendon instability in the carpal tunnel or the condition of surrounding tissues, the method comprising the steps of detecting sound produced by tendon translation across the diameter of the carpal tunnel during repetitive hand use with a microphone, and evaluating the sound to diagnose tendon instability in the carpal tunnel and to determine the quality and quantity of tissues surrounding the tendons.

Yet another form of the invention is a method for detecting tendon translation in the carpal tunnel comprising the steps of sensing sound produced by relative movement of tendons in the carpal tunnel, one to another, in a dorsal-palmar and radial-ulnar plane during repetitive hand use, with a microphone; and using the sound to diagnose tendon instability.

BRIEF DESCRIPTION OF THE DRAWINGS

The invention is described in more detail hereinafter with reference to the accompanying drawings wherein like reference characters refer to the same parts throughout the several views and in which.

DESCRIPTION OF THE PREFERRED EMBODIMENT

Figure 3:
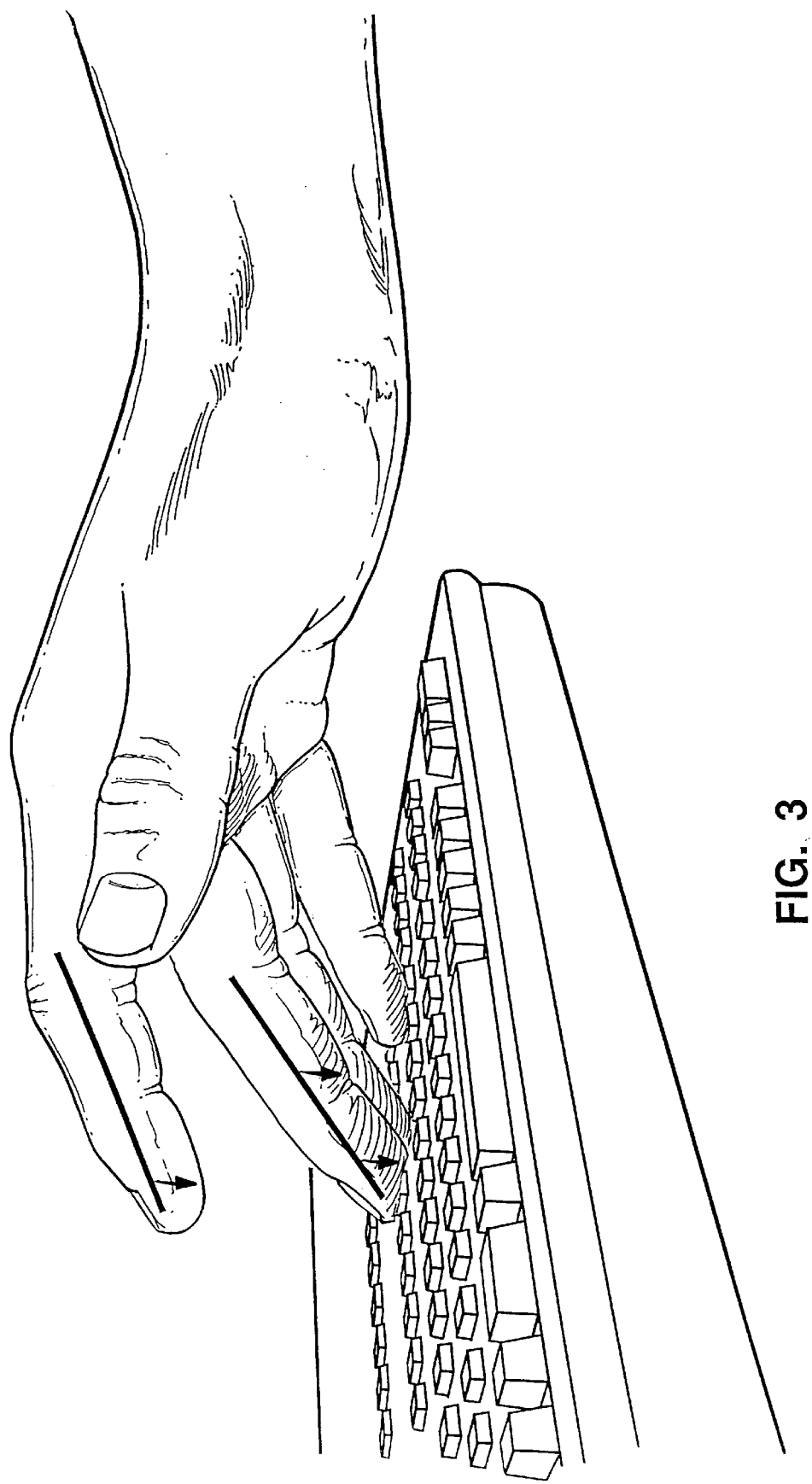
FIG. 3 is a perspective view showing typical flat fingers typing on a conventional electronic keyboard.

The foundation of the present invention is the recognition that so called idiopathic carpal tunnel syndrome, particularly as it occurs in keyboard operators, is a result of the way in which keyboard operators strike the keys. Typically, many subjects form habits of using the fingers with the distal joint extended so that the keys are pressed with the palmar aspect of the pulp of the finger (shown in FIG. 3), rather than with its palmar-distal tip. This "habit", along with a minimal actuation force requirement of the "modern" computer keyboard, allows the relatively singular contraction of one of the extrinsic muscle tendon units, while leaving other extrinsic muscle tendon units relatively or absolutely relaxed as they pass through the carpal tunnel. The resulting translation of this singular tendon produces shear stresses at the interface between adjacent tendons and their associated synovial membranes. In the acute stages, the cyclic shear stress would cause an acute edema formation, and a transient rise in carpal tunnel pressures, with secondary clinical signs and symptoms of carpal tunnel syndrome. Repeated episodes would produce increasing degrees of edema formation and an associated cellular transudate with proteinaceous materials in the interstitial spaces, progressively being converted into inelastic "fibrous tissue", i.e., an evolutionary process of the development of scar formation. This entire process could be visualized as a progressive transformation of the thin elastic synovial membrane into a more edematious, thickened, and less compliant structure. Pathophysiologically, this would cause an increase in carpal tunnel pressures paralleled by the clinical development of carpal tunnel syndrome and its known signs and symptoms. At first, it would be a cyclic increase and decrease in carpal tunnel pressure as the edema fluid would accumulate and then dissipate as a function of the level of injury to the synovium. With the persistent shear stresses induced by carpal tunnel tendon instability, the thickening would progressively increase, thereby producing a constant increase in carpal tunnel pressures and an established clinical case of carpal tunnel syndrome.

Figure 14:
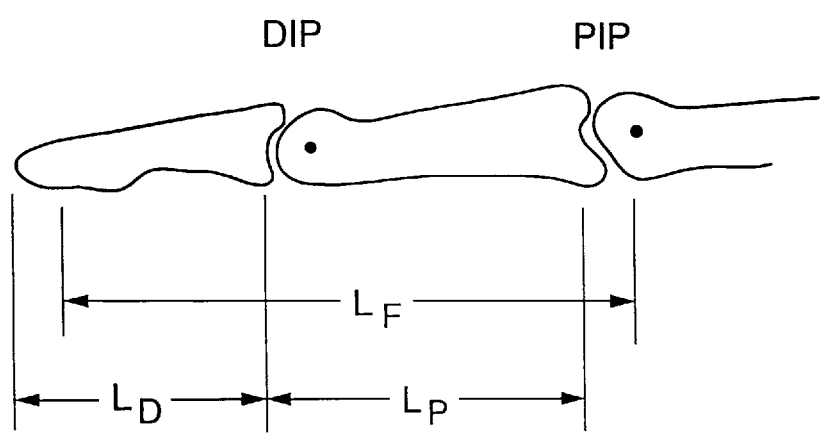
FIG. 14 is a diagram illustrating a finger with PIP and DIP joints.

The selection of an appropriate key actuation force can be determined from the anatomical dimensions of the distal joints of the fingers, along with the strength of the flexor digitorum sublimus (FDS) muscle tendon unit as it acts at the proximal interphalangial (PIP) joint. In terms of carpal tunnel tendons, the individual is mainly using the FDS muscle tendon unit with the intrinsic muscles (flexor digitorum profundus electrically and mechanically silent) to depress a key, keeping the distal interphalangial (DIP) joints relatively extended. The forces are transmitted through the DIP joints to the pulp at the tip of the distal phalanx, via the DIP joint capsular ligaments and volar plate. The distal and middle phalanx act as one "rigid" structure, with key actuation powered by the FDS muscle tendon unit only. A simple way to inhibit this hand use pattern is to require forces greater than the FDS and intrinsic muscles can provide alone, without exceeding the combined capability of the FDS and FDP muscles. The total mechanics in the digits are very complex, but in this case as described above, a simple analysis based on the geometry and FDS tendon forces should be sufficient. L. D. Ketchum from measurements in vivo, estimated the maximum tendon force capability in 40 individuals, as reported in "A clinical study of forces generated by the intrinsic muscles of the index finger and the extrinsic flexor and extensor muscles of the hand", The Journal of Hand Surgery, November 1978, vol. 3, No. 6, pp. 571–578, incorporated herein by reference. He also measured the joint moment arms in 10 fresh frozen cadavers. The remaining anatomical data for the calculation is described by G. T. Lin in "Functional anatomy of the human digital flexor pulley system", The Journal of Hand Surgery, November 1989 vol. 14A, No. 6, pp. 949–956, incorporated herein by reference. Lin measured bone lengths in a radiographic study of 10 hands. These measurements of bone length can be used to approximate the distance from the PIP joint center of rotation to the middle of the pad of the distal phalanx (see FIG. 14).

The analysis is that of a simple structure with forces creating moments about the PIP joint center of rotation. If a force perpendicular to the axis of the phalanx is assumed, the equation for the key force capability can be derived and is described as follows and is calculated in the table:

| Key force = FDS tendon force × PIP moment arm/ (DP length + MP length) | | | | |
|---|---|---|---|---|
| Finger | DP length mm | MP length mm | FD moment mm | FDS Force Kg | Key Force Kg |
| Index | 18.73 | 24.03 | 8.3 | 6.91 | 1.34 |
| Long | 18.61 | 28.00 | 8.7 | 7.63 | 1.42 |
| Ring | 18.48 | 26.04 | 8.5 | 6.21 | 1.19 |
| Little | 16.85 | 18.57 | 7.4 | 3.73 | 0.78 |

Based on this nominal data, the desired key force for actuation would be in the range of one kilogram. Even though this is an average case, in reality, individuals with lesser or greater strength would find it difficult or impossible to type using the FDS alone with this level of force required.

Figure 1:
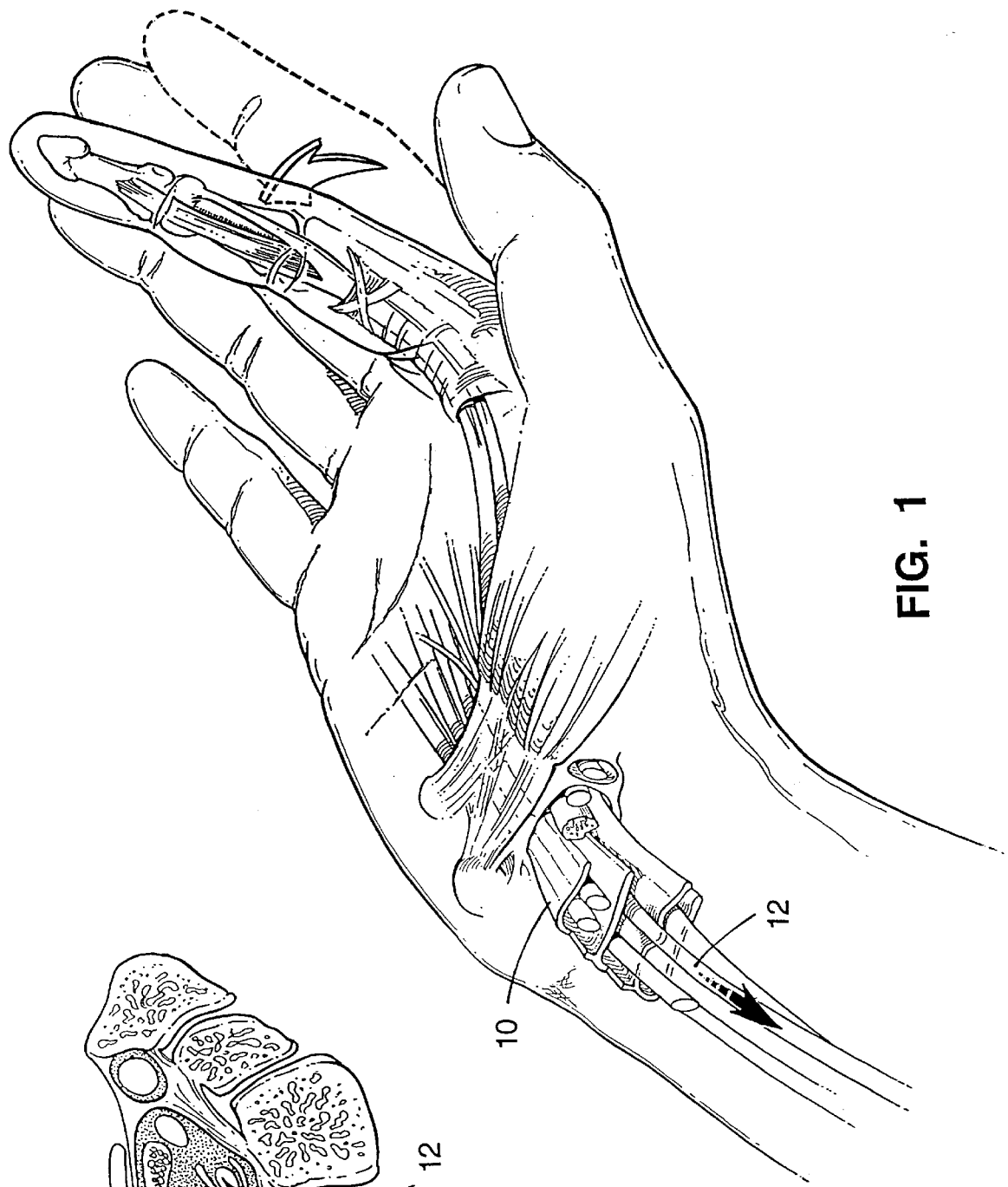
FIG. 1 is a partially cut-away perspective view of a hand showing the various tendons in the hand which control finger and thumb movement.
Figure 2:
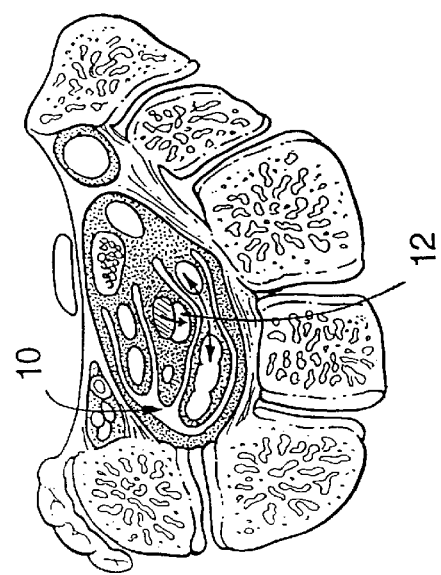
FIG. 2 is a cross-sectional view through the carpal tunnel showing dorsal displacement of the sublimis tendon during its muscle's contraction.
Figures 4, 5:
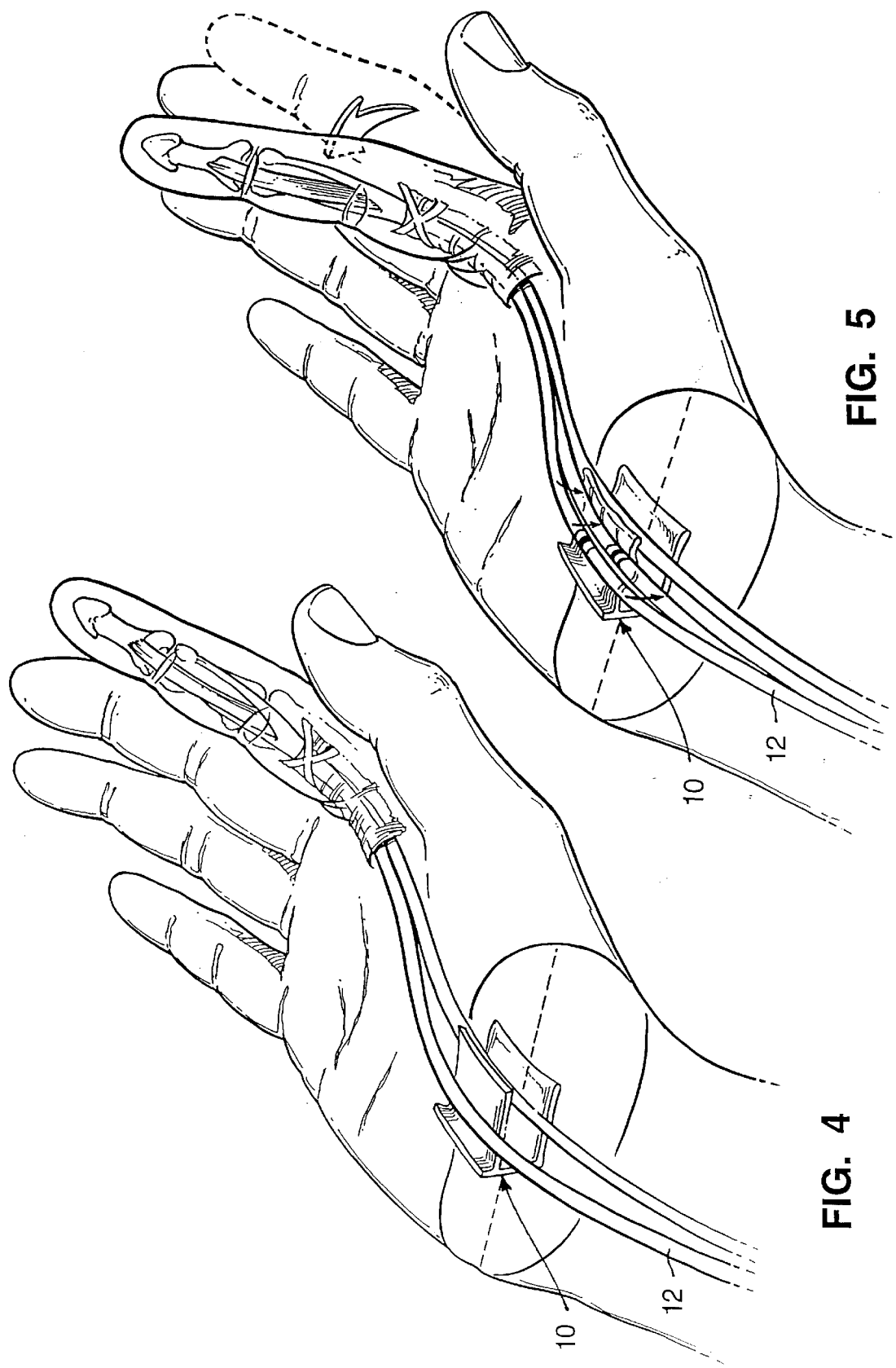
FIGS. 4 and 5 show a sublimis tendon in the hand before and during muscle contraction, respectively.
Figure 6:
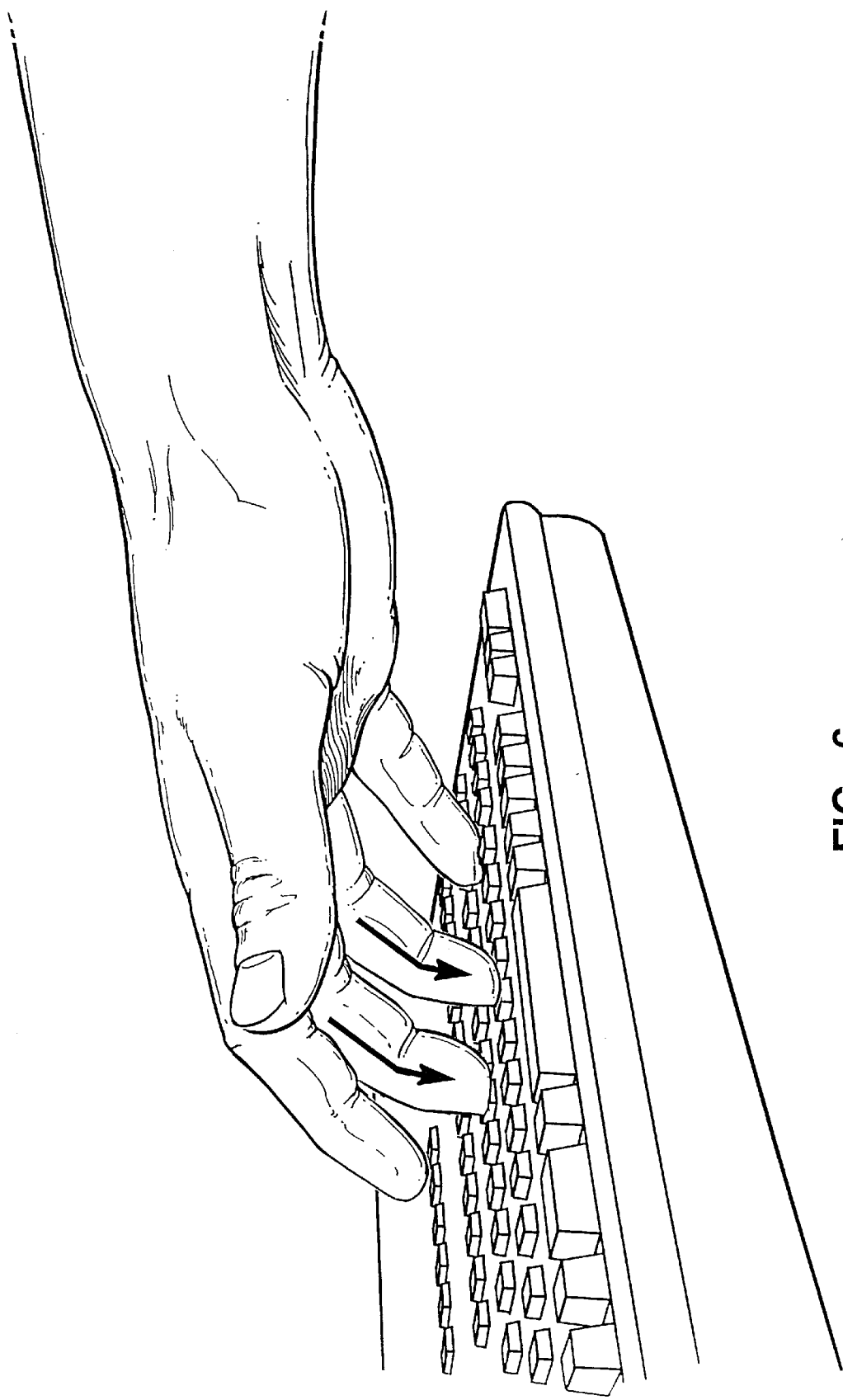
FIG. 6 is a perspective view showing an operator's finger position when using a keyboard structure of this invention.

By way of further description of the drawings, FIG. 1 illustrates the tendons in the hand which pass through the carpal tunnel within a tendon sheath (ulnar bursa) 10. Tension on the sublimis tendon 12 causes dorsal movement of the tendon and subjects the interposed synovium (i.e., the "tendon sheath") to shear forces which can result in micro trauma. FIG. 2 is a cross-sectional view through the carpal tunnel showing the manner in which tension on the sublimis tendon 12 causes dorsal movement of the tendon and subjects the tendon synovium (sheath) to shear forces. This phenomenon is also illustrated in FIGS. 4 and 5.

Figure 7A:
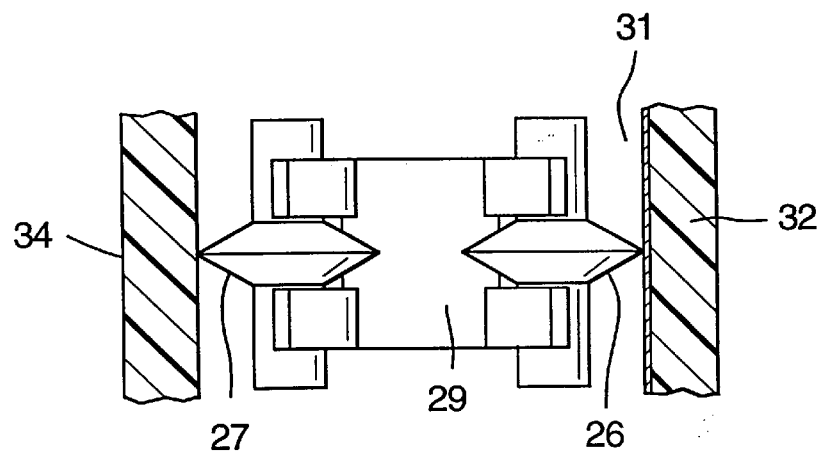
FIG. 7A is a cross-sectional view of the construction shown in FIG. 7 taken along line 7A—7A.
Figure 7:
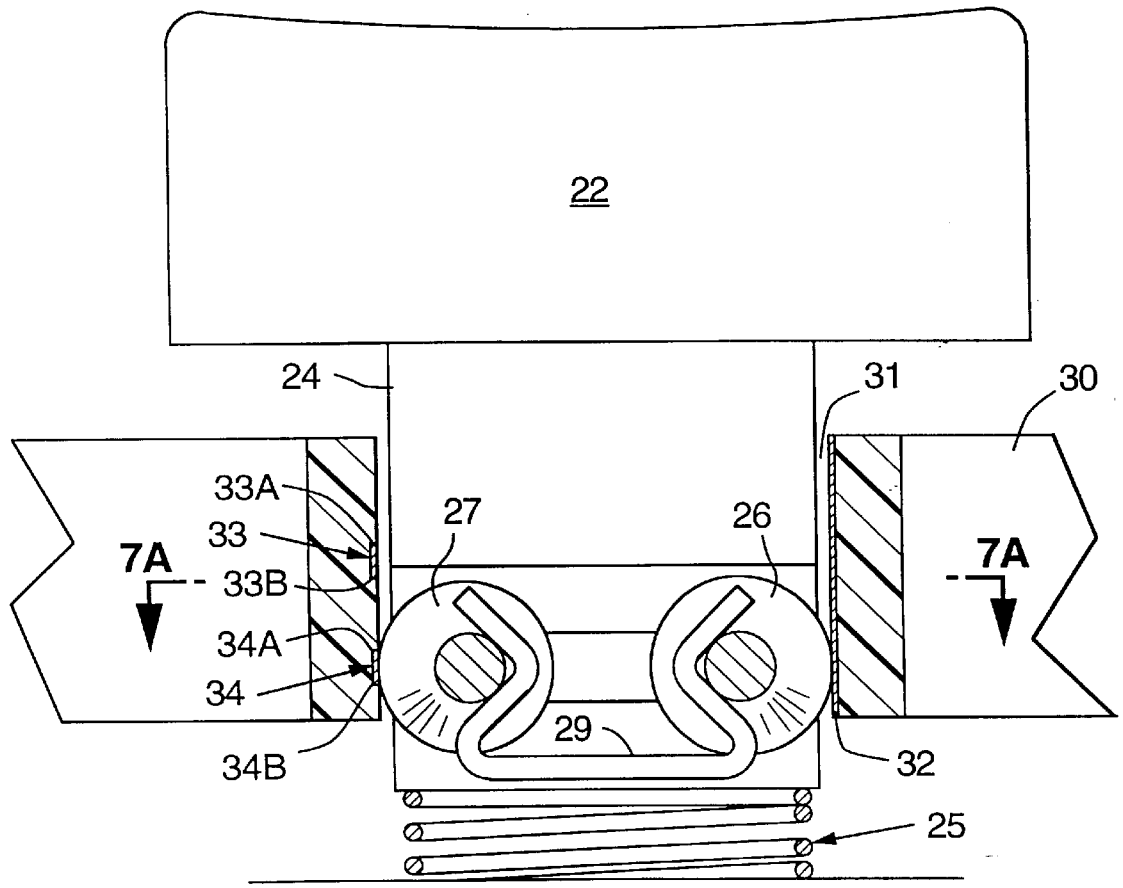
FIG. 7 is a side elevational view of one embodiment of key pad construction useful in this invention.

FIGS. 7 and 7A are side elevational and cross-sectional views, respectively, of on embodiment of key pad construction 20 of the invention comprising a key pad 22 supported on the upper end of a rod or body portion 24. A coil return spring 25 is positioned beneath the lower end of rod 24 to urge or bias the rod and key pad to its normal raised position, as shown. The rod 24 is able to move along a vertical axis in aperture 31 in board 30 of a keyboard construction. On one side or wall of the aperture 31 includes an electrically-conductive plate or surface 32 which is connected to ground. The opposite wall or face of the aperture includes two switches 33 and 34.

Carried by rod 24 are conductive rollers 26 and 27 which are urged away from opposite sides of rod 24 by conductive separation spring 29. As the force on key pad 22 forces rod 24 downwardly, roller 26 stays in contact with the ground surface 32. When roller 27 contacts the upper edge 33A of switch element 33, an electrical path is completed through switch element 33, roller 27, spring 29, roller 26 and ground surface 32. Further depression of the key pad breaks the contact with element 33 when roller 27 proceeds below edge 33B. When the key pad is depressed to a sufficient extent, another circuit is completed when roller 27 contacts the upper edge 34A of switch element 34. Further depression of the key pad breaks the contact with element 34 when roller 27 proceeds below edge 34B. Thus, the time required to move the keypad downwardly from its uppermost position to the upper and lower edges of switch 33 and then to the upper and lower edges of switch 34 can be measured precisely. That information, along with the mass of the key, enables one to calculate the force used in depressing the key.

Figure 9:
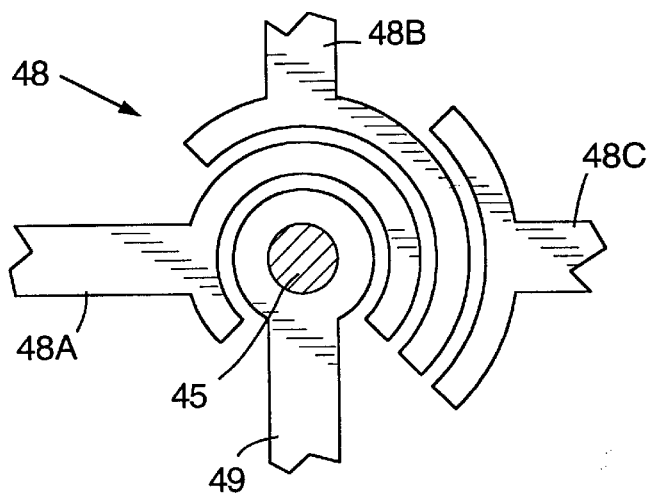
FIG. 9 is a top view of the contact pattern used in the construction of FIG. 8.
Figure 8:
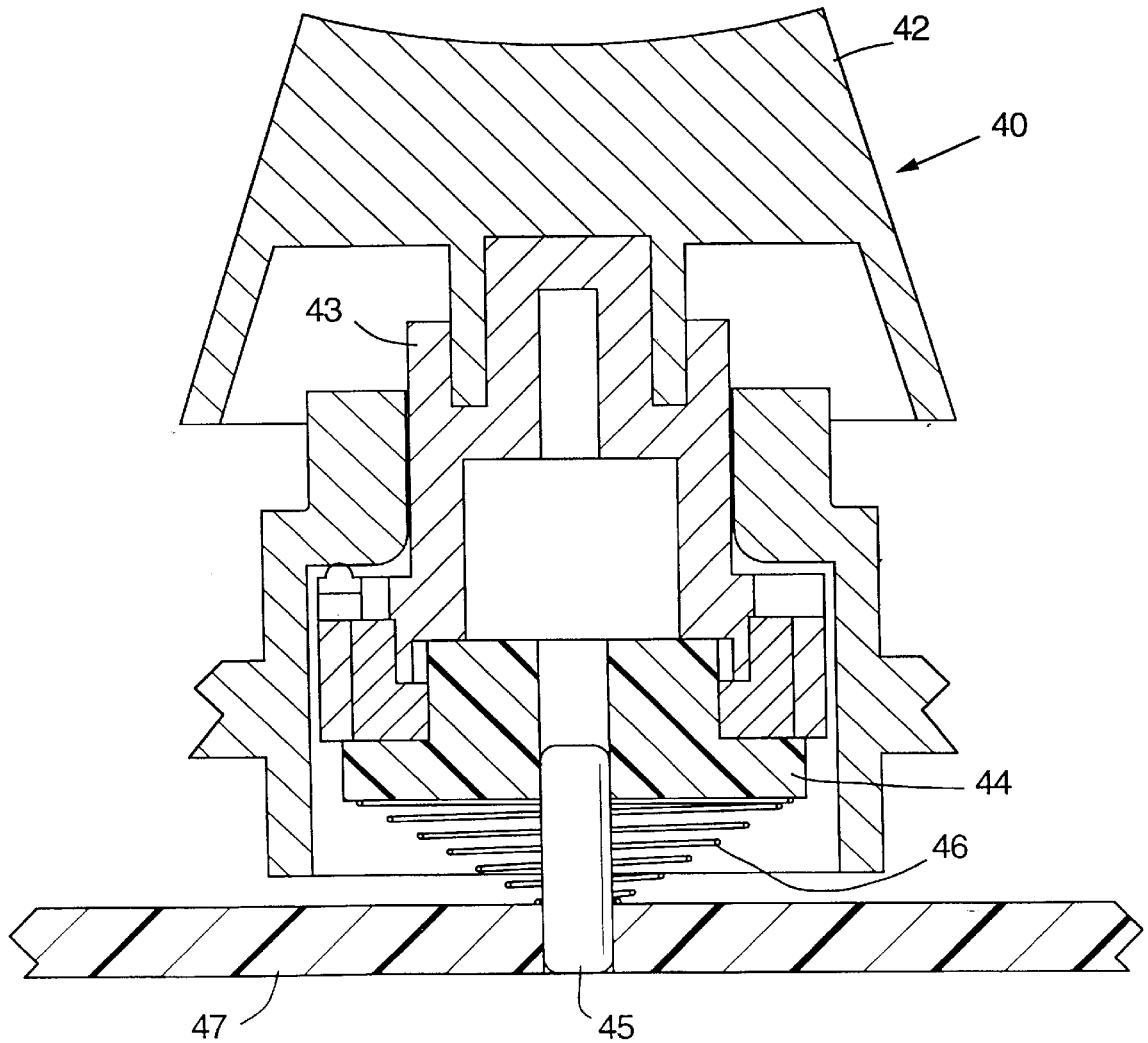
FIG. 8 is a side elevational view of another embodiment of key pad construction of the invention.

FIGS. 8 and 9 illustrate another embodiment of key pad construction 40 useful in this invention. The key construction 40 comprises key pad 42, key pad retainer 43, spring pusher 44, guide pin 45, and helical spiral coil spring 46. The guide pin is secured at its lower end in a circuit board 47. A three-switch pattern 48 is secured to the upper surface of the board and is shown in FIG. 9. As the key is depressed, the conductive coil spring 46 makes successive contact with the three switches 48A, 48B and 48C. The ground element 49 makes continual contact with the guide pin 45 and the spring.

Figure 10:
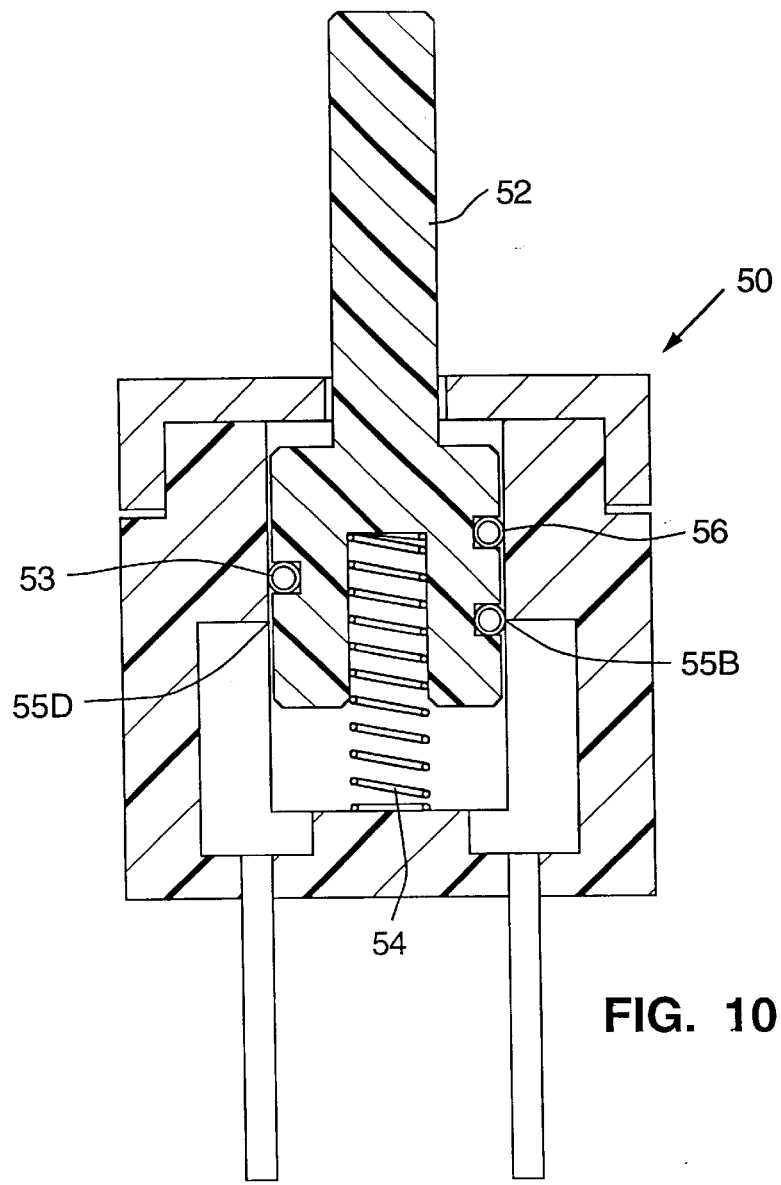
FIGS. 10 and 10A show cut-away and top views, respectively, of another embodiment of key pad construction useful in this invention.
Figure 10A:
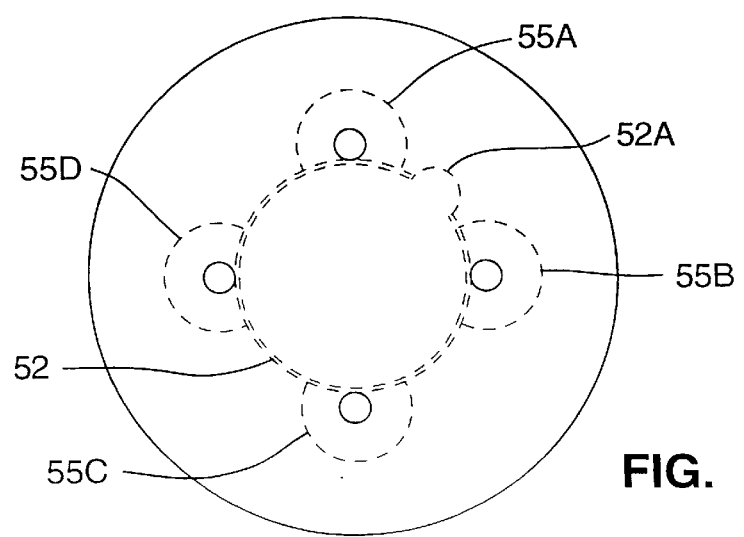

FIG. 10 is an elevational cross-sectional view of another embodiment of key construction 50 useful in this invention comprising a vertical rod or plunger 52, a compression spring 53, a return spring 54, and contacts 55. The compression spring 53 is a conventional helical coil spring which is wrapped around the rod 52 and seated in a helical groove 56. FIG. 10A is a top view of the construction showing that the rod 52 includes an anti-rotation projection 52A which fits into a vertical groove of similar shape in the housing. The four contacts 55A, B, C and D are also shown.

As the key is depressed, the spring 53 travels downward with the rod 52. A portion of the spring 53 will make electrical contact with only one of the four contacts 55 spaced around the periphery of the switch 50. That first contact 55A is the ground. As the rod 52 continues downward, each of the remaining contacts 55B, C and D will make electrical contact with the spring 53, closing a circuit with the first ground contact 55A. This movement, with the known helix angle of the groove 56 in the rod 52, acts as sequential switches at known spacing, thereby allowing measurement of the time intervals for depressing the key a defined distance.

Figure 11:
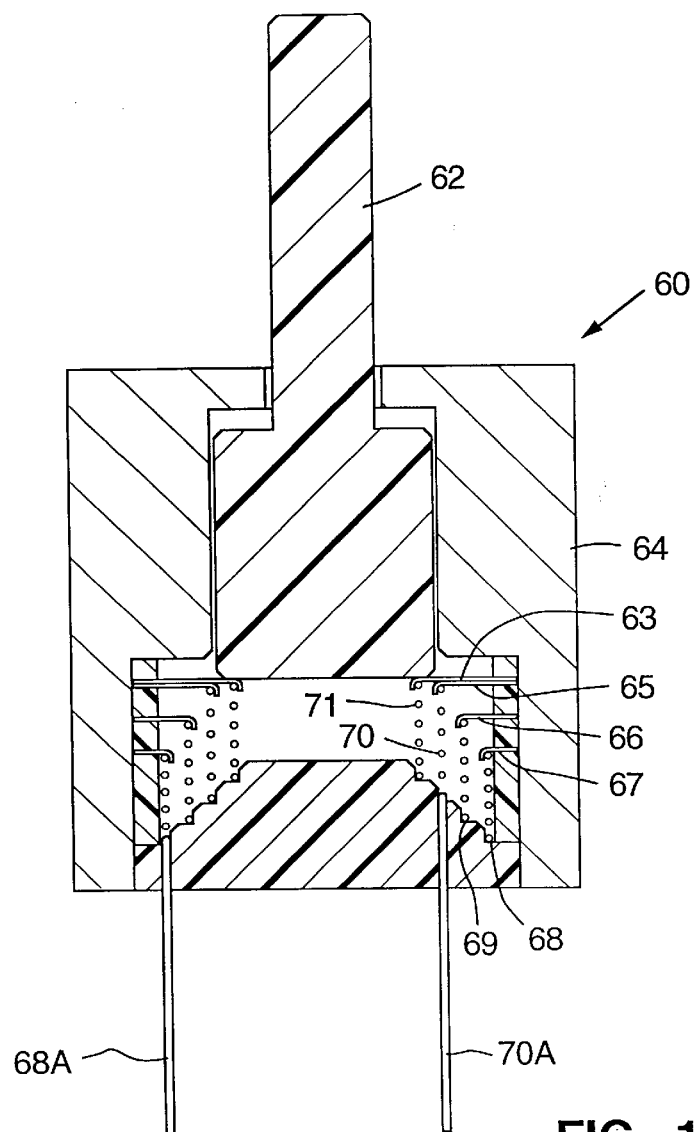
FIG. 11 is a cut-away view of another embodiment of key pad construction.
Figure 11A:
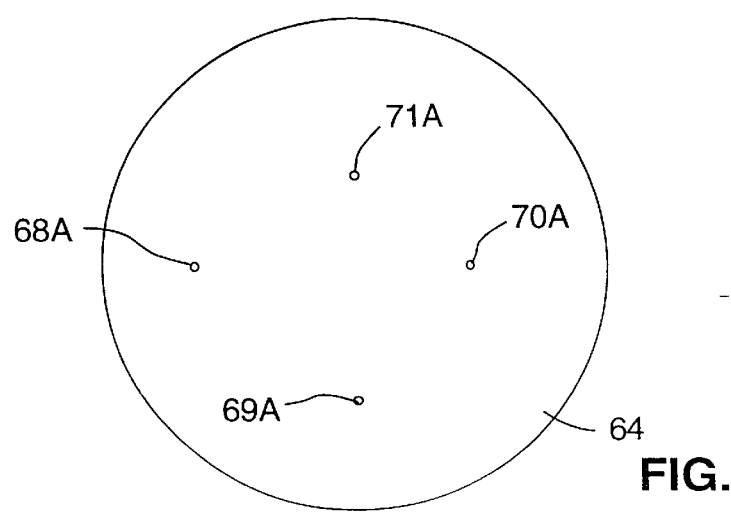
FIG. 11A is a bottom view of the embodiment of FIG. 11.

FIGS. 11 and 11A show another embodiment of key construction 60 useful in this invention comprising a vertical rod 62 which can move vertically in housing 64. A plurality of vertically spaced conductive washers 63, 65, 66, and 67 are supported beneath the lower end of rod 62 by coiled helical springs 71, 70, 69 and 68, respectively. One end of spring 68 is denoted as 68A and the opposite end is conductively secured to washer 67. Similarly, each washer is conductively secured to a respective spring which has one end (e.g., 69A, 70A, 71A) protruding from the switch body 64. As the key is depressed, washer 63 is first urged into contact with washer 65, then washer 65 is urged into contact with washer 66, and finally washer 66 is urged into contact with washer 67. This sequential movement acts as sequential switches, thereby allowing measurement of the time intervals for depressing the key a defined distance.

Figure 12:
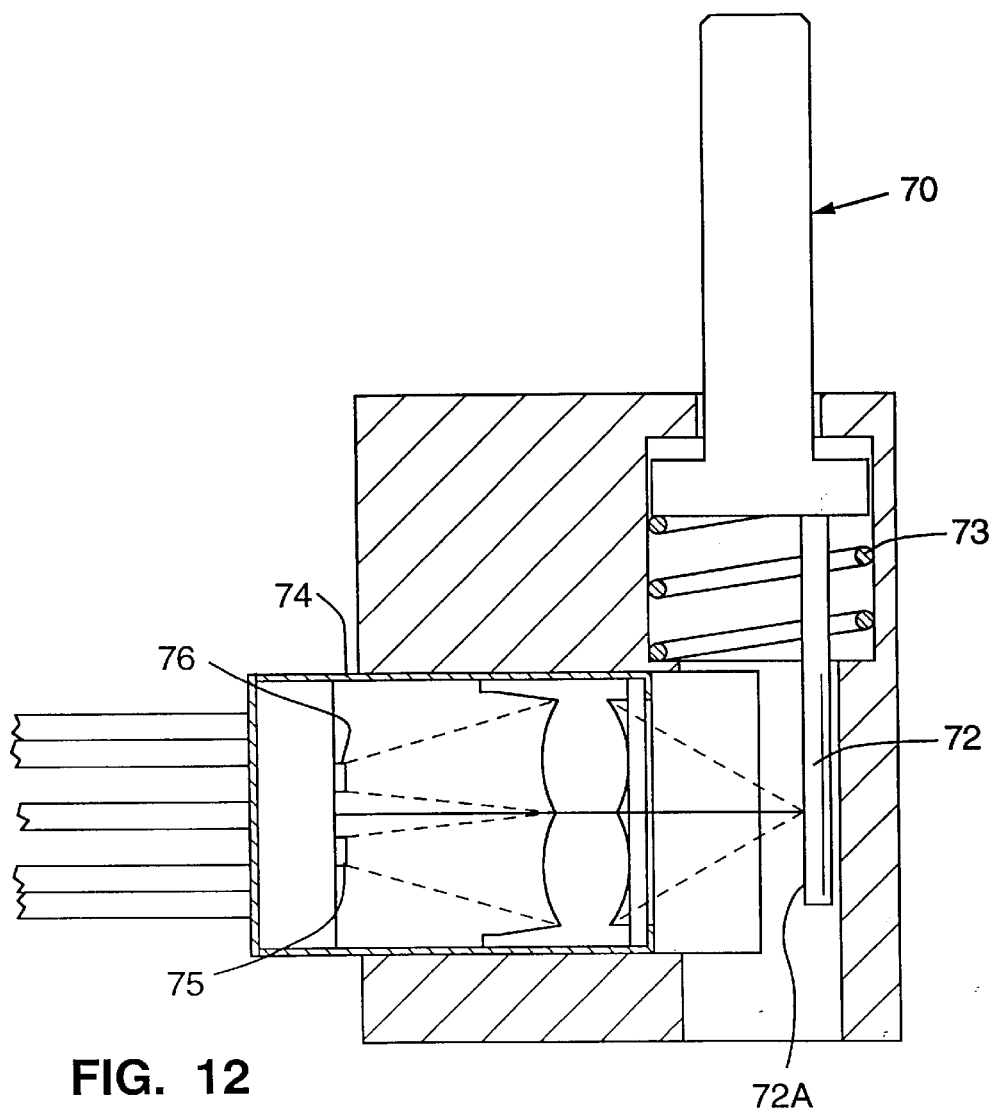
FIGS. 12 and 12A are cut-away and top views, respectively, of yet another embodiment of key pad construction useful in this invention.
Figure 12A:
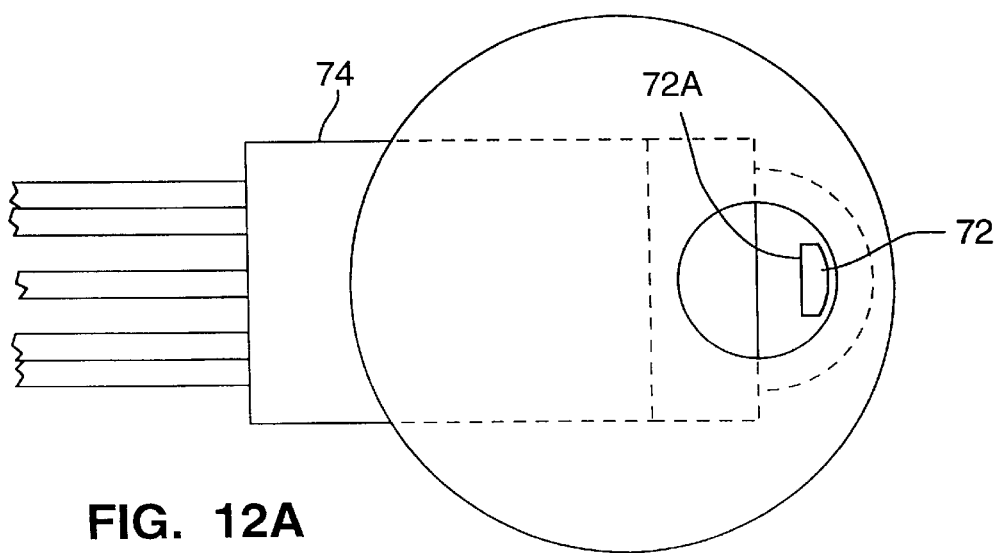

FIGS. 12 and 12A illustrate another key construction of the invention in which a key 70 includes a depending leg 72 having bar code lines on one vertical surface 72A. An optical reflector sensor 74 (comprising infrared emitter 75 and infrared detector 76) is able to detect downward movement of the key leg 72 and determine the time required to move certain distances, thereby enabling calculation of the velocity and acceleration of the key. A return spring 73 under the key biases the key to its normal uppermost position.

Figure 13:
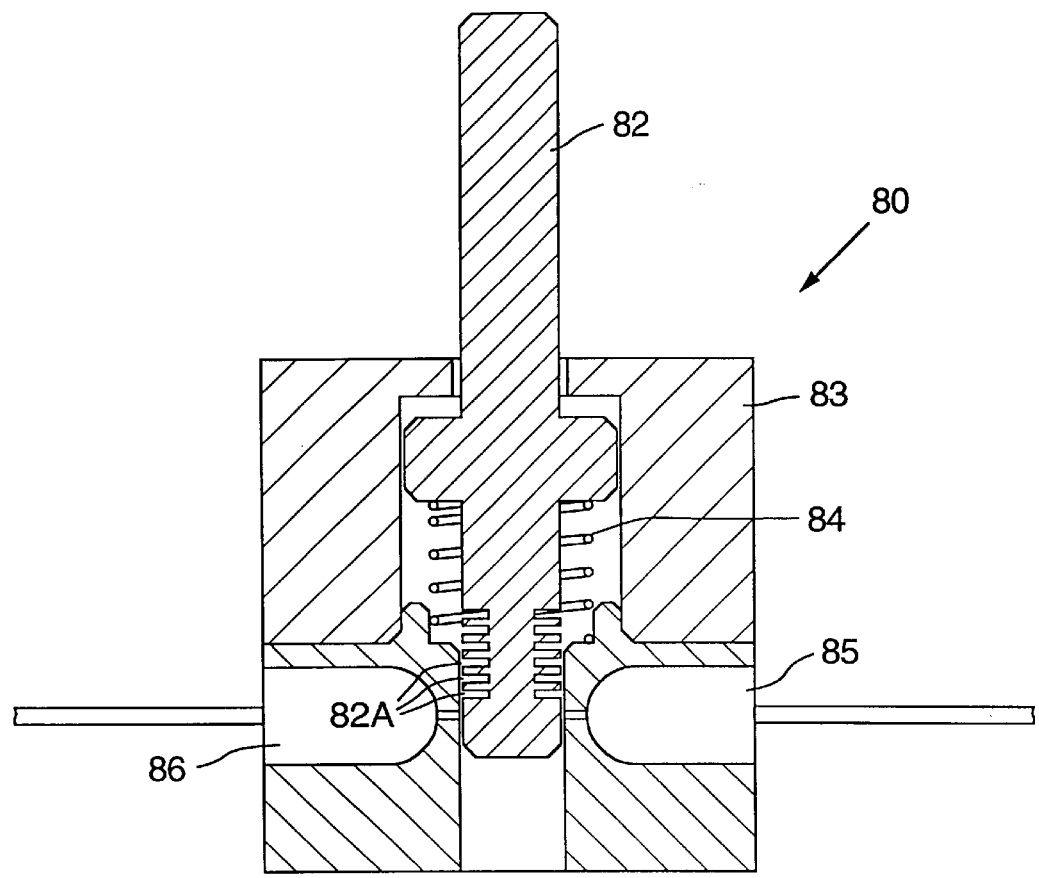
FIGS. 13 and 13A are cut-away and top views, respectively, of another embodiment of key pad construction useful in this invention.
Figure 13A:
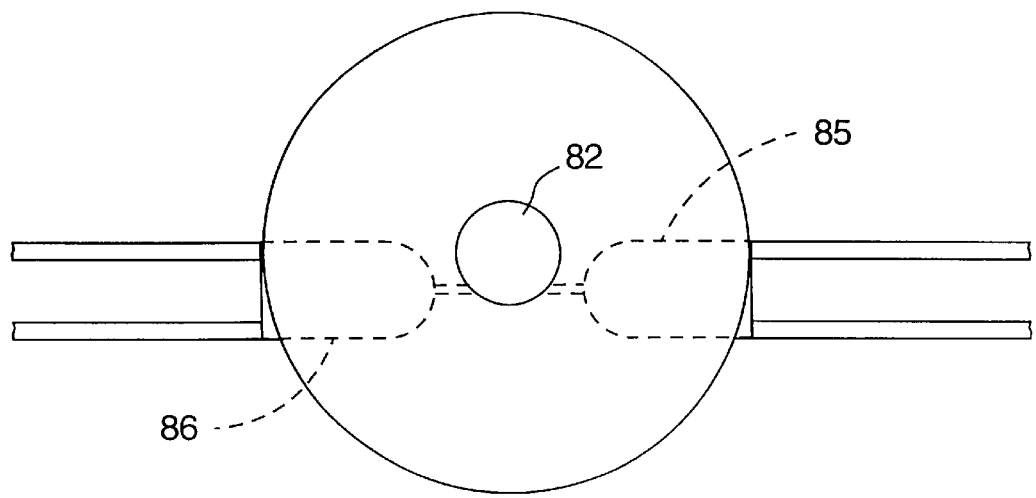

FIGS. 13 and 13A illustrate another embodiment of key construction 80 of the invention comprising key 82, housing 83, return spring 84, infrared emitting diode 85, and photodetector 86. The lower end of key 82 includes a plurality of vertically-spaced grooves 82A. As the key is depressed, the beam from the diode 85 is sequentially blocked and opened by the structure of the key and its grooves. This enables the extent, and acceleration, of depression of the key to be determined.

Other variants are possible without departing from the scope and spirit of the present invention. For example, unphysiologic tendon translation denoting tendon instability in the carpal tunnel can be determined or detected by sensing or recording the sound produced by tendon translation (e.g., during operation of a keyboard by a person, or otherwise engaging in activity involving repetitive hand motion or other hand use patterns). That is, detecting events related to unphysiologic tendon translation denoting tendon instability in the carpal tunnel can be accomplished by detecting the vibration produced by tendon motion in the carpal tunnel during hand use, and then evaluating the vibrations to diagnose tendon instability in the carpal tunnel and determine the quality and quantity of tissues, i.e. synovium, surrounding the tendons. As an example, a microphone may be used to detect the sound of tendon translation. Then the sound can be evaluated in order to diagnose tendon instability or it may be used in a system to reduce incidence of the tendon instability and therefore of carpal tunnel syndrome. Other variants are also possible.

What is claimed is:

1. A method for detecting events related to unphysiologic tendon translation denoting tendon instability in the carpal tunnel or the condition of surrounding tissues, the method comprising the steps of:

(a) detecting sound produced by tendon translation across the diameter of the carpal tunnel during repetitive hand use with a microphone; and (b) evaluating said sound to diagnose tendon instability in the carpal tunnel and to determine the quality and quantity of tissues surrounding the tendons.

2. A method in accordance with claim 1, wherein said hand use comprises operation of a keyboard by de pressing keys.

3. A method in accordance with claim 1, wherein the tissues include the synovium.

4. A method for detecting unphysiologic tendon translation denoting tendon instability in the carpal tunnel comprising the steps of sensing sound produced by tendon translation across the diameter of the carpal tunnel during repetitive hand use, with a microphone, and evaluating the sound to diagnose tendon instability.

5. A method according to claim 4 wherein the sound is sensed during operation of keyboard by a person.

6. A method for detecting unphysiologic tendon translation denoting tendon instability in the carpal tunnel comprising the steps of sensing sound produced by tendon translation across the diameter of the carpal tunnel during repetitive hand use, with a microphone, and using the sound to diagnose tendon instability or in a system to reduce incidence of the tendon instability.

7. A method according to claim 6 wherein the sound is sensed during operation of keyboard by a person.

8. A method for detecting events related to tendon translation in the carpal tunnel or the condition of surrounding tissues, the method comprising the steps of:

(a) recording sound produced by tendon translation across the diameter of the carpal tunnel during repetitive hand use, with a microphone; and (b) evaluating the recorded sound to diagnose tendon instability or in a system to reduce the incidence of tendon instability in the carpal tunnel.

9. The method of claim 8, wherein said hand use comprises operation of a keyboard by depressing keys.

10. The method of claim 8 wherein the tissues include the synovium.

11. A method for detecting tendon translation in the carpal tunnel comprising the steps of:

sensing sound produced by relative movement of tendons in the carpal tunnel, one to another, in a dorsal-palmar and radial-ulnar plane during repetitive hand use, with a microphone; and using the sound to diagnose tendon instability.

12. The method of claim 11 wherein the sound is sensed during operation of keyboard by a person.

* * * * *